United States Patent

Ulyanov et al.

[11] 3,945,242
[45] Mar. 23, 1976

[54] METHOD OF MEASURING DYNAMIC CHARACTERISTICS OF MATERIALS AND DEVICE FOR EFFECTING SAME

[76] Inventors: Lev Petrovich Ulyanov, Eropkinsky pereulok, 7, kv. 6; Oleg Nikolaevich Borisenkov, ulitsa Oktyabrskaya 24, kv. 8; Natalya Nikolaevna Kastorskaya, ulitsa Bolshaya Cherkizovskaya 5, korpus 1, kv. 69; Georgy Vladimirovich Vinogradov, ulitsa Chernyshevskogo, 41, kv. 26; Jury Grigorievich Yanovsky, ulitsa Bolshaya Serpukhovskaya, 48, kv. 11; Sergei Ivanovich Sergeenkov, ulitsa Dmitria Ulyanova, 3, kv. 123-a, all of Moscow, U.S.S.R.

[22] Filed: Aug. 13, 1973

[21] Appl. No.: 387,814

[52] U.S. Cl. .................. 73/15.4; 73/67.1; 73/99
[51] Int. Cl.² ............................................ G01N 3/32
[58] Field of Search ........... 73/15.4, 15.6, 67, 67.1, 73/67.2, 67.3, 67.4, 99, 101

[56] References Cited
UNITED STATES PATENTS

| 3,030,803 | 4/1962 | Painter | 73/67.1 |
| 3,374,662 | 3/1968 | Achter et al. | 73/67.4 |
| 3,508,437 | 4/1970 | Van Beek | 73/67.2 |
| 3,680,366 | 8/1972 | Moser et al. | 73/99 |
| 3,718,028 | 2/1973 | Moser et al. | 73/67.3 |

Primary Examiner—Richard C. Queisser
Assistant Examiner—John P. Beauchamp
Attorney, Agent, or Firm—Haseltine, Lake & Waters

[57] ABSTRACT

The method of measuring dynamic characteristics of materials consists in obtaining, in the course of measurement, a control current which ensures oscillations of a specimen of a material at a preset amplitude and frequency. Then, real and imaginary components of the control current are discriminated, and two restoring currents are generated; these currents are summated, and the total current is used to control the movement of the specimen; after that, the real and imaginary components of the control current are discriminated for the second time, and their value, as well as the values of the restoring currents and the preset amplitude and frequency of the deformation of the specimen are used to calculate dynamic characteristics of the material.

4 Claims, 7 Drawing Figures

METHOD OF MEASURING DYNAMIC CHARACTERISTICS OF MATERIALS AND DEVICE FOR EFFECTING SAME

The present invention relates to dynamic studies of materials in the infralow frequency range, and more particularly to a method of measuring dynamic characteristics of materials and a device for effecting same. Measured by means of forced oscillations of a specimen of a material are the following dynamic characteristics of materials: the modulus of elasticity, the modulus of loss due to uniform deformation, the dynamic viscosity and the dynamic loss angle.

In the prior art, there is a method of measuring dynamic characteristics of materials, for example, by means of forced torsional oscillations.

This prior-art method consists in obtaining an exciting current, which is converted into a torque and applied to a tested specimen of a material, and in subsequent measuring the angle of twist of the specimen, the amplitudes of the exciting current and of the oscillations of the specimen and the phase difference therebetween are used to calculate dynamic characteristics of the material.

A disadvantage of the prior-art method is that it is time-consuming, limits the frequency range on the side of the low frequencies (which are no less than $10^{-3}$ Hz) and fails to ensure a required accuracy of measurement.

In the prior art, there is also an apparatus for effecting the above method of measuring dynamic characteristics of a material.

This apparatus comprises an actuating coil, an infralow frequency oscillator, the voltage across the output thereof being proportional to the current energizing the actuating coil which is placed in a uniform field of a permanent magnet and is rigidly fixed to a specimen of a material placed in a thermostatic chamber provided with a temperature controller, an angle transducer with an a.c. voltage amplifier, a demodulator and an analyzer.

The voltage across the output of the infralow frequency oscillator initiates a current which flows through the actuating coil and interacts with the uniform field of the permanent magnet, producing a torque which is applied to the specimen. Under the action of the torque, the actuating coil oscillates together with the specimen; the transient being over, the oscillations acquire a sinusoidal form. By means of the angle transducer, the a.c. voltage amplifier and the demodulator, these oscillations are registered by the analyzer.

Simultaneously, with the aid of the a.c. voltage amplifier, the analyzer registers oscillations of the exciting current through the actuating coil.

A disadvantage of this prior-art apparatus is that the value of the torque which is applied to a specimen of a material to obtain an amplitude of oscillations within the linear deformation range, is unknown, which necessitates trial disturbances; that, in turn, results in a substantial waste of time, especially when working in the infralow frequency range, and also makes it difficult to process the results of measurements and prolongs transients which depend upon the properties of the specimen and the frequency of the torque.

It is an object of the present invention to provide a method of measuring dynamic characteristics of materials by means of forced oscillations of a specimen of a material in the infralow frequency range. Another object of the present invention is to provide an apparatus for effecting same.

The essence of the invention in this case is that the proposed method of measuring dynamic characteristics of materials by means of forced oscillations of a specimen of a material in the infralow frequency range consists in obtaining, according to the invention, in the course of measurement, a control current which is converted into a mechanical stress of the specimen, ensuring oscillations thereof at a preset amplitude and frequency, whereafter a real and an imaginary components of the control current are discriminated, analyzed, and two restoring currents are generated, one being in phase and commensurable with the real component of the control current, whereas the other is in phase and commensurable with the imaginary component of the control current, then the control current and the two restoring currents are summated, and the total current, which is converted into a mechanical stress of the specimen, serves to control the movement of the latter, whereafter the real and imaginary components of the control current are discriminated for the second time, and the values of the components of the control current, the values of the restoring currents and the preset frequency and amplitude of the deformation of the specimen of a material are used, with due consideration to the shape of the specimen, to calculate dynamic characteristics of the material, since the sum of the real components of the control and restoring current is proportional to the dynamic modulus of elasticity, while the sum of the imaginary components of the control and restoring currents is proportional to the dynamic modulus of losses.

The invention also resides in that the proposed apparatus for effecting the above method of measuring dynamic characteristics comprises an actuating coil made of a wire in the form of a loop with a mirror attached thereto, which is placed in a uniform field of a permanent magnet, a thermocryostatic chamber with a program temperature controller, a specimen of a material and two holders which adjust the specimen inside the thermocryostatic chamber, a rod, a normal stress compensator secured by means of the rod to a holder of the specimen and, through that holder, to one end of the specimen, whereas the other end of the specimen is rigidly fixed by means of its second holder and a second rod to the actuating coil, and infralow frequency oscillator electrically connected to the actuating coil and to an analyzer, a prism, two differentially connected photocells optically associated via the prism with the mirror of the actuating coil, an a.c. voltage amplifier connected to the two differentially connected photocells, and a demodulator connected to the a.c. voltage amplifier, the essential feature of the apparatus being that, in accordance with the invention, the actuating coil with the mirror attached thereto, the prism, the two differentially connected photocells, the a.c. voltage amplifier and the demodulator make up a closed follow-up circuit which also comprises a galvanometer with a mirror, placed in the uniform field of the permanent magnet together with the actuating coil, the mirror of the galvanometer being optically associated with that of the actuating coil, an optical modulator, a laser optically associated via the optical modulator and the mirror of the actuating coil with the mirror of the galvanometer, the common load of the two differentially connected photocells coupled to the a.c. voltage amplifier, a d.c. voltage amplifier connected to the demodulator and the analyzer, a buffer amplifier connected to the d.c. voltage amplifier, a summing amplifier connected to the buffer amplifier and the actuating coil, whereas the infralow frequency oscillator having an output with a stabilized zerophase voltage thereacross is incorporated into a means for setting the amplitude and frequency of oscillations of the specimen, which also comprises a precision attenuator connected to the galvanometer and also coupled to the output of the infralow frequency oscillator, with a stabilized zero-phase voltage thereacross, the infralow frequency oscillator presetting the frequency of electric oscillations and the precision attenuator, their amplitude.

It is expedient that the infralow frequency oscillator having an output with a stabilized zero-phase voltage thereacross and the actuating coil be incorporated into an open circuit for proportional control of the movement of the actuating coil, which circuit also incorporate a second precision attenuator, a summing amplifier connected to the actuating coil and, via the second precision attenuator, to the output of the infralow frequency oscillator with a stabilized zero-phase voltage thereacross; it is also expedient that the infralow frequency oscillator having another output with a stabilized voltage across displaced in phase by 90° with respect to the stabilized zero-phase voltage and the actuating coil make up another open circuit for proportional control of the movement of the actuating coil, which circuit also incorporates a third precision attenuator and a summing amplifier connected to the actuating coil and, via the third precision attenuator, to the output of the infralow frequency oscillator, the stabilized voltage whereacross is displaced in phase by 90° with respect to the stabilized zero-phase voltage.

The application of the proposed method of measuring dynamic characteristics of materials and the device for effecting same substantially reduces operator man hours and expands the tested frequency range, which has made it possible to solve such classical problems as checking the method of the superposition of temperature and time, i.e. checking the equivalence of variations in dynamic characteristics of materials due to a disturbance frequency, on the one hand, and the temperature of materials, on the other.

The present invention permits of testing materials at temperatures ranging from −100°C to +300°C with an accuracy of ±0.5°C and at frequencies ranging from 1.0 to $10^{-6}$ Hz.

The invention will now be explained in greater detail with reference to embodiments thereof taken in conjunction with the accompanying drawings, wherein.

Figure 1:
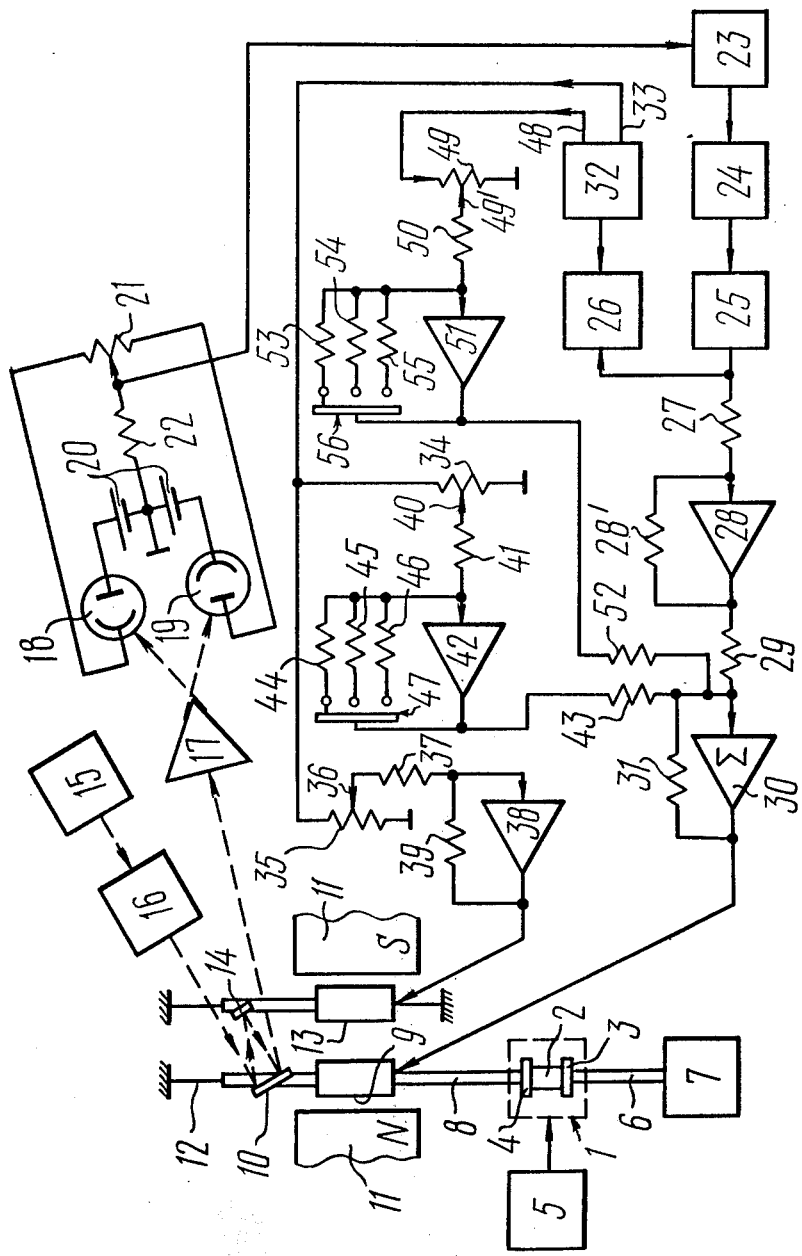
FIG. 1 is a block diagram of a device for effecting the proposed method of measuring dynamic characteristics, in accordance with the invention.

Consider now the proposed method of measuring dynamic characteristics of materials.

The behavior of specimens of materials, for example, due to shearing strains resulting from torsional oscillations is generally described by the following formula:

$$\tau\theta'' + A\cdot\eta(\theta',\theta)\cdot\theta' + A\cdot G(\theta',\theta)\cdot\theta = M(t) \qquad (1)$$

where
$\tau$ is the main central moment of inertia,
$\theta$ is the angle of deflection of a specimen of a material with respect to its equilibrium position (the angle of twist of a specimen),
A is the shape factor of a specimen of a material,
$\eta(\theta', \theta)$ is the dynamic viscosity of a material,
$G(\theta', \theta)$ is the dynamic modulus of elasticity of a material,
$t$ is time,
$M(t)$ is the disturbing moment (the torque).

With small relative shearing strains, when there is a linear dependence of the deformation of a specimen of a material upon an applied mechanical stress, the equation (1) assumes the following form:

$$\tau\theta'' + A\cdot\eta(\theta')\cdot\theta' + A\cdot G(\theta')\cdot\theta = M(t) \qquad (2)$$

Changes in the relationships between $\eta(\theta')$ and $G(\theta')$ are measured with the aid of a harmonic analysis by means of forced oscillations of the specimen at a frequency $\omega$.

Now the equation of the movement of the specimen takes the following form:

$$\tau\theta'' + A\cdot\eta(\omega)\theta' + AG(\omega)\theta = M\sin(\omega t + \phi_0) \qquad (3)$$

where
$\theta$ is the amplitude of oscillations of the specimen and
$\phi_0$ is the initial phase angle of the disturbing moment.

In accordance with the invention, a control current is obtained and is converted into a mechanical stress of the specimen, for example, into a torque $M(t)$ which ensures oscillations of the specimen at a preset amplitude $\alpha$ and frequency $\omega$, through comparing actual oscillations $\theta(t)$ of the specimen to preset oscillations $\alpha\sin\omega t$ i.e. the torque.

$$M(t) = K[\alpha\sin\omega t - \theta(t)] \qquad (4)$$

where $k$ is the proportionality constant.

In the infralow frequency range, with $f \leq 1.0$ Hz, the presence of the term of inertia $\tau\theta''$ in the equation (3) is ignored due to its small value; now the equation of the movement of the specimen assumes the following form:

$$\eta\theta' + G\theta = k(\alpha\sin\omega t - \theta) \qquad (5)$$

where
$\eta = A\eta(\omega)$
$G = AG(\omega)$
$\theta = \theta(t)$
or $$\frac{\eta}{K}\theta' + \frac{G+\eta}{K}\theta = \alpha\sin\omega t \qquad (5')$$

Integrating this equation, we obtain the following:

$$\theta = \frac{\alpha K \omega \eta}{(G+K)^2+\eta^2\omega^2} \phi - \frac{G+K}{\eta} t +$$

$$+ \frac{K\alpha}{(G+K)^2+\eta^2\omega^2}[(G+K)\sin\omega t - \omega\eta\cos\omega t] \quad (6)$$

where $$\frac{\alpha K \omega \eta}{(G+\eta)^2+\eta^2\omega^2} \phi - \frac{G+K}{\eta} t = \theta \text{ damped},$$

and $$\frac{K\alpha}{(G+K)^2+\eta^2\omega^2}[(G+K)\sin\omega t - \omega\eta\cos\omega t] = \theta \text{steady-state}$$

The attenuation time constant of the transient is $$\tau = \frac{\eta}{G_0+K} \quad (7)$$

If we assume, for example, that $k = 200\ \omega\eta$ and G is of any value, then $$\tau \leq \frac{\eta}{200\eta\omega},$$

and $$\frac{\eta}{200\eta\omega+G} = \frac{1}{200\omega} = \frac{1}{200\cdot 2\pi f} = \frac{T}{200\cdot 2\pi} < 10^{-3}T,$$

i.e. $\tau < 10^{-3}T$ \quad (8)

where T is the period of forced oscillations of the specimen.

Thus, $\tau < 10^{-3}T$, i.e. the attenuation time constant of the transient of stabilizing forced harmonic oscillations is less than $10^{-3}$ of a period T of preset oscillations.

The attenuation term $\theta$ damped of the equation, under these conditions, has a maximum amplitude with $t = 0$.

$$\theta \text{ damped max} = \frac{\alpha K \omega \eta}{(G+K)^2+\eta^2\omega^2} < 5\cdot 10^{-3}\alpha \quad (9)$$

assuming that $k = 200\ \eta\omega$.

Thus, forced angular oscillations of the specimen are stabilized practically instantaneously.

For $\theta$ steady-state we have:

$$\theta \text{ steady-state} = \frac{K\alpha}{(G+K)^2+\eta^2\omega^2}[(G+K)\sin\omega t$$

$$- \omega\eta \cos \omega t] \quad (10)$$

$$\theta \text{ steady-state} = \frac{\alpha K \sqrt{(G+K)^2+\omega^2\eta^2}}{(G+K)^2+\eta^2\omega^2}\sin(\omega t+\phi) \quad (11)$$

where $$\phi = \text{arc } tg\left(-\frac{\omega\eta}{G+K}\right).$$

In this case, the amplitude error $\xi$ is proportional to the difference between the preset and actual amplitudes of oscillations.

$$\xi = \frac{\alpha-\theta}{\alpha} = \frac{\alpha - \alpha\frac{\sqrt{K\ (G+K)^2+\omega^2\eta^2}}{(G+K)^2+\eta^2\omega^2}}{\alpha} =$$

$$= 1 - \frac{K}{\sqrt{(G+K)^2+\omega^2\eta^2}}; \quad (12)$$

With $k = 200\ \omega\eta$, $\xi$ 0.0013, i.e., it does not exceed 0.13 percent. This means that the amplitude of oscillations of the specimen $\theta$ is equal, with an error of 0.13 percent, to the present amplitude of oscillations $\alpha$.

The phase error is equal to the difference between the phases of the preset oscillations, whose phase is assumed to be equal to 0°, and those of oscillations of the specimen, whose phase is equal to arctg $$\left(-\frac{\omega\ \eta}{G+K}\right)$$

$$\xi\phi = \theta - \text{arc } tg\left(-\frac{\omega\ \eta}{G+K}\right) \quad (13)$$

With $k = 200\ \omega\eta$. $\xi\phi \leq 0.005$ radn $\approx 17'$.

This means that the oscillations of the specimen lag behind the preset oscillations in phase by $17'$.

Under steady-state conditions, the specimen is acted upon by a torque equal to $M_{steady\text{-}state}$.

$$M \text{ steady-state} = \left[K\alpha - \frac{K^2\alpha(G+K)}{(G+K)^2+\eta^2\omega^2}\right]\sin\omega t +$$

$$+ \frac{K^2\alpha\ \omega\ \eta}{(G+K)^2+\eta^2\omega^2}\cos\cdot\omega t \quad (14)$$

If we neglect the phase and amplitude errors, $\xi\alpha$ and $\xi\phi$, i.e. if we assume that $k \to \infty$, the equation (14) will assume the following form:

$$M \text{ steady-state} = -\alpha G \sin\omega t + \alpha\omega\eta\cos\omega t \quad (15)$$

The control current Iy is proportional to the steady-state moment.

$$I_y = K_1 M_{steady\text{-}state} \quad (16)$$

or $$I_Y = K_1(-\alpha G\sin\delta t + \alpha\omega\eta\cos\omega t) \quad (17)$$

The real and imaginary components of the control current are discriminated. To generalize, $$I_y{}^* = -K_1 G + K_1 j\alpha\omega\eta \quad (18)$$

where $K$, $\alpha G$ is the real component of the control current and $jk\alpha\omega\eta$ is the imaginary component of the control currnet; the real and imaginary components of the control current are analyzed and, to reduce measurement errors, two restoring currents, $Ik_1$ and $jIk_2$, are generated, one being in phase and commensurable with the real component of the control current, while the other is in phase and commensurable with the imaginary component of the control current; then, the currents Iy, $Ik_1$ and $jIk_2$ are summated, and a total current is obtained:

$$I_{\nu\Sigma}^* = I_{K_1} + jI_{K_2} + (I_\nu + I_{K_1} - jI_{K_2}) \quad (19)$$

The total current $I_\Sigma^*$ is converted into a mechanical stress of the specimen and is used to control the movement of the latter. After that, the real and imaginary components of the control current, $Iy_1$ and $jIy_2$, are discriminated for the second time $$I_{\nu_1}^* = I_\nu - I_{K_1} - I_{K_2} = -K_1\alpha G + jK_1\alpha\omega\eta - I_{K_1} - jI_{K_2} = I_{\nu_1} + jI_{\nu_2} \quad (20)$$

Substituting Eq. (20) into (19), we obtain the following:

$$I_2^* = I_\nu^* = I_{K_1} + jI_{K_2} + I_{\nu_1} + jI_{\nu_2} = (I_{K_1} + I_{\nu_1}) + j(I_K + I_{\nu_2}) \quad (21)$$

The values of the components $Iy_1$ and $Iy_2$ of the control current, the values of the restoring currents $Ik_1$ and $jIk_2$ and the preset frequency and amplitude of the deformation of the specimen are used, with due consideration to the shape A of the specimen, to calculate dynamic characteristics of the material.

Substituting the value of $I_\nu^*$ from Eq. (18) in Eg. 21, we obtain:

$$-K_1\alpha G + j\alpha\omega\eta = (I_{K_1} + I_{\nu_1}) + j(I_{K_2} + I_{\nu_2}) \quad (22)$$

Thus, $$-K_1\alpha G = I_{K_1} + I_{\nu_1}$$
$$-K_1\alpha\omega\eta = I_{K_2} + I_{\nu_2} \quad (23)$$

Substituting the values of $\eta$ and G from Eq. (5), we obtain:

$$-K_1\alpha AG(\omega) = I_{K_1} + I_{\nu_1}$$
$$K_1\alpha\omega A(\omega) = I_{K_2} + I_{\nu_2} \quad (24)$$

From this, the dynamic modulus of elasticity $G(\omega)$ of the material is obtained:

$$G(\omega) = \left| \frac{I_{K_1} + I_{\nu_1}}{K_1\alpha A} \right| \quad (25)$$

the dynamic loss modulus $\omega\eta(\omega)$ of the material:

$$\omega\eta(\omega) = \left| \frac{I_{K_2} + I_{\nu_2}}{K_1\alpha A} \right| \quad (26)$$

the dynamic viscosity of the material:

$$\eta(\omega) = \left| \frac{I_{K_2} + I_{\nu_2}}{K_1 A} \right| \quad (27)$$

the loss angle tangent:

$$\tan\delta = \frac{\omega\eta(\omega)}{G(\omega)} = \left| \frac{I_{K_2} + I_{\nu_2}}{I_{K_1} + I_{\nu_1}} \right| \quad (28)$$

The use of two restoring currents raises the accuracy of measurements and the range of relationships between the modulus of elasticity of a material under measurement and the loss modulus of that material, i.e.

$$\frac{\omega\eta(\omega)}{G(\omega)} = tg\,\delta$$

where $\delta$ is the loss angle.

This results in a greater number of dynamic moduli of materials being measured and, consequently, in an enlarged class of materials to be measured. Here and elsewhere in the present description, the term "class" denotes a group of materials with the utmost diversity of dynamic characteristics.

Consider, for example, a polymer, say, polybutadiene with the value $$\frac{\omega_o \eta(\omega_o)}{G(\omega_o)} = tg\,\delta = 100,$$

where $\omega_o$ is a certain measurement frequency, for example, $\omega_o = 0.1$. In the course of measurement, a control current is obtained and converted into a mechanical stress of a specimen of polybutadiene to ensure oscillations thereof at an amplitude that differs from the preset one, for example, by 0.5 percent; therewith, a real and imaginary components of the control current are discriminated with an error of, say, ±1 percent which is adjusted to the value of the control current. Under these conditions, the real component of the control current is not determined with a sufficient accuracy, as the real component of the control current, which is proportional to the dynamic modulus of elasticity $G(\omega_o)$, in our example constitutes 0.01 of the imaginary component of the control current, which, in turn, is proportional to the loss modulus $\omega_o\eta(\omega_o)$ and is equal to 0.01 of the total control current, whereas the total error of measuring the total control current in this example equals to 1 percent + 0.5 percent = 1.5 percent, or 0.015 of the control current; the imaginary component is determined with an error of 1.5 percent. A restoring current $jIk_2$ is generated, which is in phase with the real component of the control current $Iy$ and is equal, for example, to 0.99 of the value of the imaginary component of control current; these currents are summated $$I_\Sigma = jI_{K_2} + (I_\nu - jI_{K_2}) = jI_{K_2} + I_\nu'$$

and the total current $I\Sigma$ converted into a mechanical stress which is applied to the specimen of polybutadiene, is used to control the movement of that specimen, therewith, the real and imaginary components of the control current $Iy_1$ and $jIy_2$ are discriminated for the second time.

$$Iy' = Iy_1 + jIy_2$$

With the same control error of 0.5 percent, in our example $Iy_1 = jI_2$, as the value of the real component $Iy_1$ remains unchanged after the introduction of the restoring current $jIk_2$ and is equal, according to our assumption, to 0.01 of the imaginary component of the control current, $jIy_2$. The error of measuring the components $Iy_1$ and $jIy_2$ equals $$\frac{I_\nu'}{I_{\nu_1}} \cdot 1\% = \frac{\sqrt{I_{\nu_1}^2 + jI_{\nu_2}^2}}{I_{\nu_1}} \cdot 1\% = \sqrt{2\%} \approx 1.4\%.$$

the real component of the total current $Iy_1$ is determined with an error of 1.9 percent, while the imaginary component is determined with an error of the determination of $j/k_2$, for example, 0.1 percent. Thus, in our example the relation of dynamic moduli tg $\delta = 100$ is measured with an error of no more than 2 percent (0.02), and the loss angle $\delta$ error is equal to $$\frac{0.02}{100} = 2 \cdot 10^{-4} \approx 1.4'$$

Consider now the proposed apparatus for effecting the above method of measuring dynamic characteristics of materials, for example, for measuring dynamic characteristics of polymers.

The apparatus for effecting the above method of measuring dynamic characteristics of polymers comprises a thermocryostatic chamber 1 containing a specimen 2 of a polymer fixed by holders 3 and 4. The thermocryostatic chamber 1 is coupled to a program temperature controller 5.

The lower holder 3 of the specimen is attached by a rod 6 to a compensator 7 of normal stresses which occur as a result of changes in the temperature of the specimen 2.

The upper holder 4 of the specimen is coupled by a rod 8 to an actuating coil 9 with a mirror 10 attached thereto. The actuating coil 9 is made of a wire in the form of a loop and is placed in a uniform field of a permanent magnet 11 by means of a suspension 12.

In the uniform field of the permanent magnet 11, there is also a galvanometer 13 with a mirror 14.

The mirror 10 of the actuating coil 9 is optically associated with a laser 15 via an optical modulator 16 to obtain a highly collimated beam modulated by a higher frequency. Said mirror 10 is also optically associated with the mirror 14 of the galvanometer 13 and, via a prism 17 made at a critical angle, with photocells 18 and 19 to obtain a voltage which is proportional to the difference between rotation angles of said galvanometer 13 and said actuating coil 9. The critical angle of the prism is indispensable for a complete reflection of a beam.

The differentially connected photocells 18 and 19 are energized by a d.c. current source 20 with a central tap and are connected via a potentiometer 21 to a common load resistor 22. The potentiometer 21 and the common load resistor 22 make up a common load of the two differentially connected photocells 18 and 19.

Connected to said common load resistor 22 is an a.c. voltage amplifier 23 with the purpose of amplifying the voltage proportional to a difference between the rotation angles of said galvanometer 13 and the actuating coil 9.

The output of said a.c. voltage amplifier 23 is connected to a demodulator 24 in order to obtain a voltage of a preset frequency. The output of said demodulator 24 is connected to the input of a d.c. voltage amplifier 25 with circuits for amplitude and phase correction of the voltage proportional to the control current flowing through the actuating coil 9.

The output of said d.c. voltage amplifier 25 is connected to an analyzer 26 and, via a resistor 27, to an operational amplifier 28, whose feedback circuit includes a resistor 28'.

Said operational amplifier 28 with the resistor 27 at its input and the resistor 28' in its feedback circuit make up a buffer amplifier used for matching the input and output electric circuits.

The output of the operational amplifier 28 is connected via a resistor 29 to the input of a summing amplifier 30 with a resistor 31 in its feedback circuit for transmitting thereto a voltage proportional to said control current. The output of the amplifier 30 is connected to the actuating coil 9 to apply the control current to the actuating coil 9.

Said galvanometer 13 with the mirror 14, said mirror 10 of the actuating coil 9 optically associated with the laser 15 via the optical modulator 16 and also optically associated with the mirror 14 of the galvanometer 13, the prism 17, the two differentially connected photocells 18 and 19 with the common load resistor 22, which are optically associated via the prism 17 with the mirror 10 of the actuating coil 9, the series-connected a.c. voltage amplifier 23 connected to the common load resistor 22, demodulator 24, buffer amplifier, summing amplifier 30 and the actuating coil 9 make up a closed follow-up circuit.

The apparatus for measuring dynamic characteristics of polymers also has an infralow frequency oscillator 32, connected thereto is the analyzer 26 to generate reference voltage.

Connected to an output 33 of said infralow frequency oscillator 32 are precision potentiometers 34 and 35. A cursor 36 of the potentiometer 35 is connected via a resistor 37 to the input of an operational amplifier 38 with a resistor 39 in its feedback circuit.

Said potentiometer 35, the resistor 37 and the operational amplifier 38 with the resistor 39 in its feedback circuit make up a precision attentuator.

Said infralow frequency oscillator 32 with the output 33 with a stabilized zero-phase voltage thereacross and said precision attenuator make up a means for setting the amplitude and frequency of oscillations of the specimen 2.

Connected to the output of the operational amplifier 38 is the galvanometer 13 for obtaining oscillations of a preset amplitude and frequency.

A cursor 40 of the potentiometer 34 is connected via a resistor 41 to an operational amplifier 42 which is connected via a resistor 43 to the summing amplifier 30. One of resistors 44, 45 and 46 is connected to the feedback circuit of the amplifier 42 via a switch 47.

Said potentiometer 34, the resistor 41, the operational amplifier 42, the resistors 44, 45 and 46 connected to the feedback circuit of the amplifier 42 via a switch 47 make up a second precision attentuator.

Said infralow frequency oscillator 32 with the output 33 with a stabilized zero-phase voltage thereacross, said second precision attenuator, said summing amplifier 30 and said actuating coil 9 make up an open circuit for proportional control of the movement of the actuating coil 9.

Connected to an output 48 of the infralow frequency oscillator 32 is a potentiometer 49 whose cursor 49' is connected via a resistor 50 to an amplifier 51 coupled via a resistor 52 to the summing amplifier 30. One of resistors 53, 54 and 55 is connected to the feedback circuit of the amplifier 51 via a switch 56.

Said potentiometer 49 resistor 50, operational amplifier 51, and resistors 53, 54 and 55 connected to the feedback circuit of the amplifier 51 via the switch 56 make up a third precision attenuator.

Said infralow frequency oscillator 32 with the output 48, the stabilized voltage whereacross is displaced in phase by 90° with respect to the stabilized zero-phase voltage, said third precision attenuator, said summing amplifier 30 and said actuating coil 9 make up a second open circuit for proportional control of the movement of the acctuating coil 9.

Figure 2:
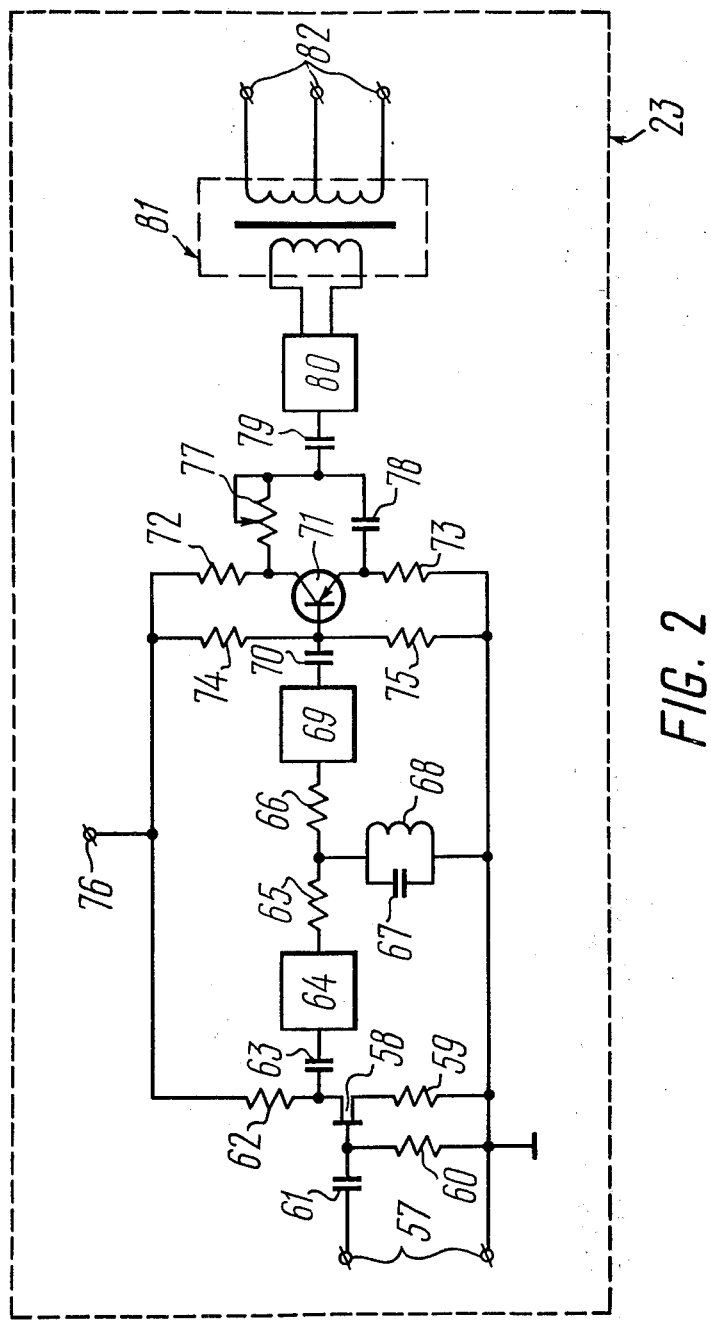
FIG. 2 is an electric circuit of the a.c. voltage amplifier of the device, in accordance with the invention.

Connected to the common load resistor 22 of the differentially connected photocells 18 and 19 is an input 57 (FIG. 2) of the a.c. voltage amplifier 23. The input stage of the a.c. voltage amplifier 23 comprises a field-effect transistor 58 with an automatic bias resistor 59, a grid leak resistance 60, a separating capacitor 61 and a load resistor 62. The load resistor 62 is connected via a separating capacitor 63 to an a.c. voltage amplifier 64. The transistorized a.c. voltage amplifier 64 is connected via a selective circuit. comprising series-connected resistors 65, 66 and a capacitor 67 and an inductance coil 68 connected in parallel, to a transistorized a.c. voltage amplifier 69.

Connected to the output of the a.c. voltage amplifier 69 via a separating capacitor 70 is a phase shifter comprising a transistor 71 with two load resistors 72 and 73. The base of the transistor 71 is connected to a voltage divider incorporating resistors 74 and 75. Connected to a terminal 76 is the negative terminal of a power source (not shown).

Connected to the resistors 72 and 73 are a series-connected rheostat 77 and capacitor 78, respectively, which are also connected via a separating capacior 79 to a transistorized a.c. amplifier 80.

Figure 3:
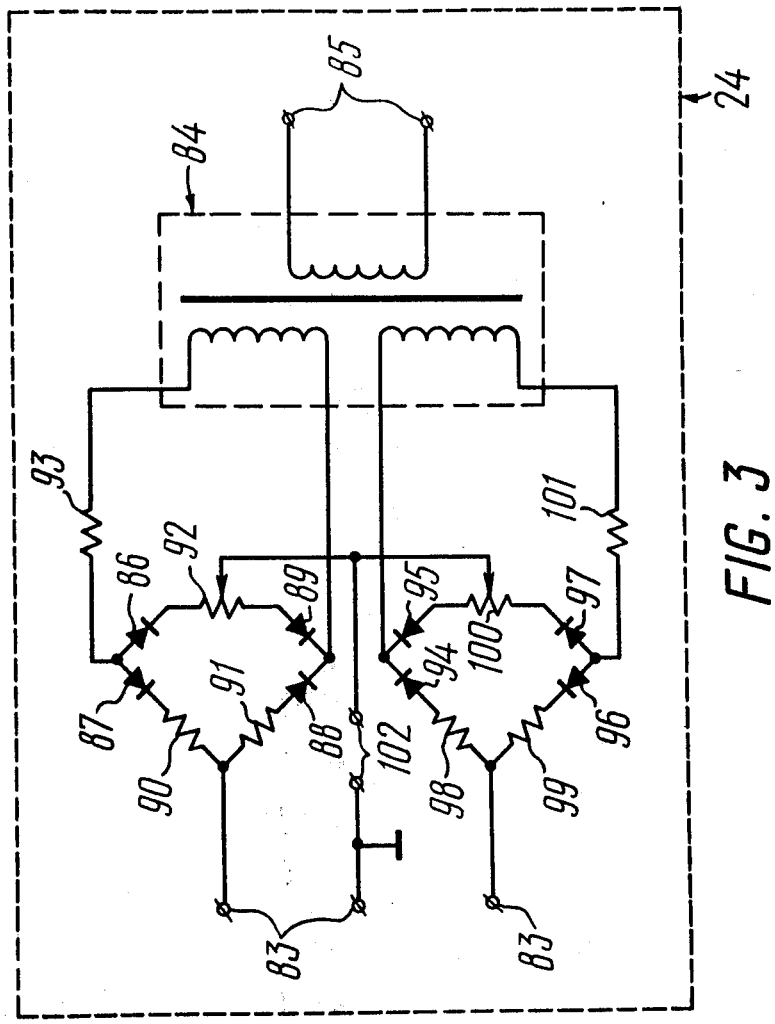
FIG. 3 is an electric circuit of the demodulator of the device, in accordance with the invention.

Connected to the output of the a.c. amplifier 80 is a transformer 81 with output terminals 82, connected whereto are input terminals 83 (FIG. 3) of the demodulator 24.

The demodulator 24 comprises two identical four-arm diode bridges and a transformer 84 connected via terminals 85 to a reference generator (not shown). One bridge, comprising diodes 86, 87, 88 and 89, two resistors 90 and 91 and a potentiometer 92, is connected to the transformer 84 via a ballast resistor 93. The other bridge, comprising diodes 94, 95, 96 and 97, two resistors 98 and 99 and a potentiometer 100, is connected to the transformer 84 via a ballast resistor 101. Cursors of the potentiometers 92 and 100 are interconnected and coupled to an output 102 of the demodulator 24.

Figure 4:
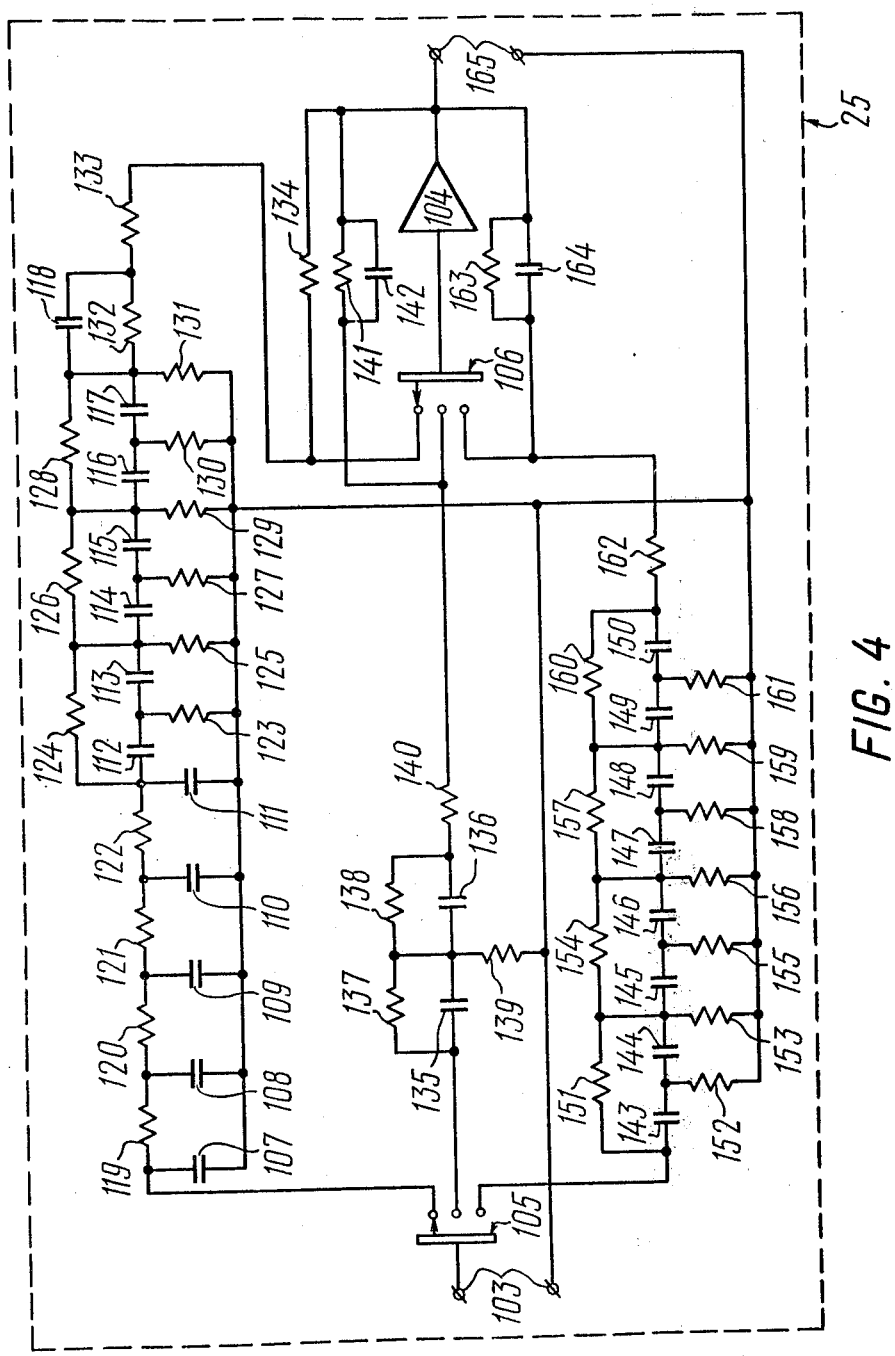
FIG. 4 is an electric circuit of the d.c. voltage amplifier of the device, in accordance with the invention.

Also connected to the output 102 of the demodulator 24 is an input 103 (FIG. 4) of the d.c. voltage amplifier 25 with amplitude-and-phase correction circuits.

The d.c. voltage amplifier 25 comprises an operational amplifier 104 and three amplitude-and-phase correction circuits commutated by switches 105 and 106 fitted on one axle.

Figure 5:
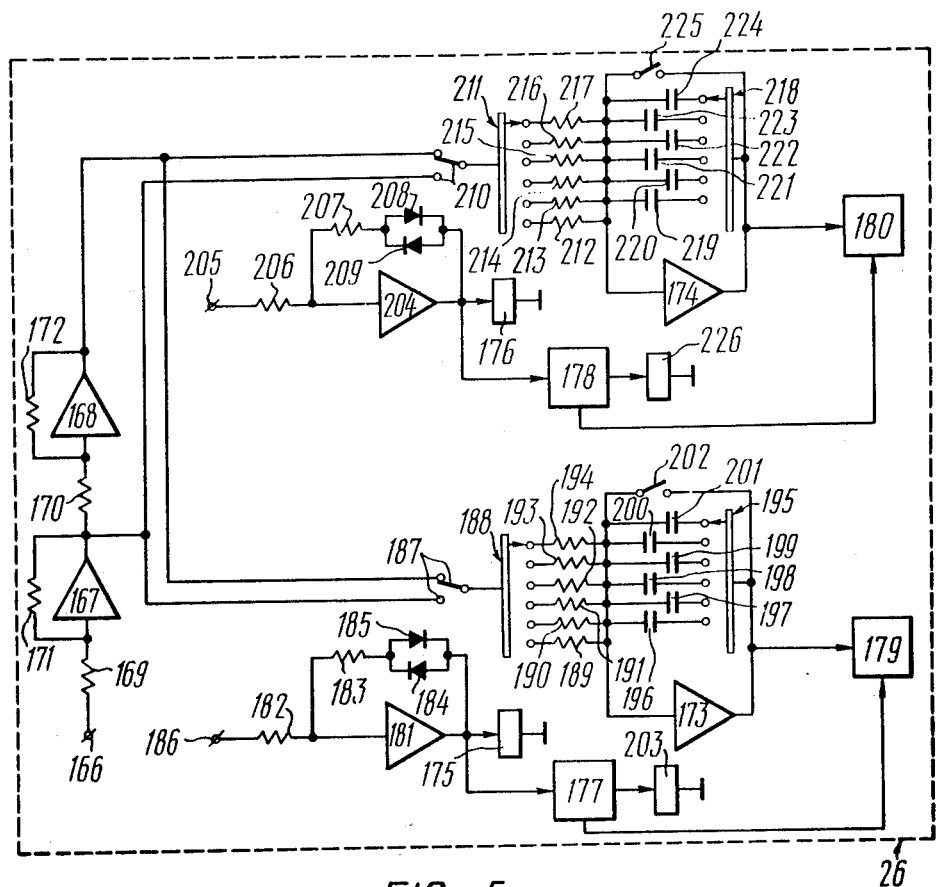
FIG. 5 is an electric circuit of the analyzer of the device, in accordance with the invention.

An amplitude-and-phase correction circuit for fluid polymers comprises capacitors 107, 108, 109, 110, 111, 112, 113, 114, 115, 116, 117, 118 and resistors 119, 120, 121, 122, 123, 124, 125, 126, 127, 128, 129, 130, 131, 132, 133 in the input circuit of the operational amplifier 104 and a resistor 134 in its feedback circuit. The amplitude-and-phase correction circuit for solid polymers comprises capacitors 135, 136 and resistors 137, 138, 139, 140 in the input circuit of the operational amplifier 104 and a resistor 141 and a capacitor 142, connected in parallel, in its feedback circuit. The amplitude-and-phase correction circuit for elastic polymers comprises capacitors 143, 144, 145, 146, 147, 148, 149, 150 and resistors 151, 152, 153, 154, 155, 156, 157, 158, 159, 160, 161, 162 in the input circuit of the operational amplifier 104 and a resistor 163 and a capacitor 164, connected in parallel in its feedback circuit. An output 165 of the d.c. voltage amplifier 25 is connected to an input 166 (FIG. 5) of the analyzer 26 and, via the resistor 27, to the input of the amplifier 28 (FIG. 1).

The analyzer 26 (FIG. 5) comprises two matching seriesconnected operational amplifiers 167 and 168 with resistors 169 and 170 in their input circuits and resistors 171 and 172 in their feedback circuits, respectively, two integrators identically incorporating operational amplifiers 173 and 174, two direct-conversion receivers incorporating relays 175 and 176, two counters 177 and 178 and two digital voltmeters 179 and 180.

The relay 175 is connected to the output of an operational amplifier 181 with an input resistor 182 and a circuit comprising a resistor 183 connected in series with two semiconductor diodes, which are in series opposition in its feedback circuit performing the function of a null indicator, whose input 186 is connected to the output 33 (FIG. 1) of the oscillator 32 with a stabilized zero-phase voltage thereacross.

Contacts 187 (FIG. 5) of the relay 175 are connected to the operational amplifiers 167 and 168 and to a switch 188, alternately connected whereto are resistors 189, 190, 191, 192, 193 and 194 of the input circuit of the operational amplifier 173. Alternately connected to the feedback circuit of the operational amplifier 173 via a switch 195 are capacitors 196, 197, 198, 199, 200 and 201 which discharge through contacts 202 of a relay 203 connected to the counter 177 of alternations of the voltage of the oscillator 32.

Connected to the operational amplifier 173 is the digital voltmeter 179 coupled to the counter 177 to synchronize the starting of the digital voltmeter 179.

The relay 176 is connected to an operational amplifier 204 which performs the function of a null indicator, whose input 205 is connected to the output 48 (FIG. 1) of the oscillator 32 stablized voltage whereacross is displaced in phase by 90° with respect to the stabilized zero-phase voltage. The input circuit of the operational amplifier 204 (FIG. 5) comprises a resistor 206, while its feedback circuit incorporates a resistor 207 connected in series with semiconductor diodes 208 and 209 which are connected in parallel opposition.

Contacts 210 of the relay 176 are connected to the operational amplifiers 167 and 168 and to a switch 211, alternately connected whereto are resistors 212, 213, 214, 215, 216 and 217 in the input circuit of the operational amplifier 174. Alternately connected to the feedback circuit of the operational amplifier 174 via a switch 218 are capacitors 219, 220, 221, 222, 223 and 224 which discharge through contacts 225 of a relay 226 connected to the counter 178.

Connected to the operational amplifier 174 is the digital voltmeter 180 which is also connected to the counter 178.

The infralow frequency oscillator 32 (FIG. 1) comprises a driving oscillator 227 (FIG. 6), connected whereto is a synchronous motor 228 which is mechanically linked through a multiple reduction gear 229 to a rotary sine-cosine transformer 230. A stator winding 231 of the rotary sine-cosine transformer 230 is shorted out, while another stator winding 232 is connected to an oscillator 233 with a stabilized amplitude. A rotor winding 234 of the rotary transformer 230 is connected to a demolulator 235 which is coupled to the generator 233 and has the output 33 (FIG. 1) with a stabilized zero-phase voltage thereacross. A rotor winding 236 (FIG. 6) of the rotary transformer 230 is connected to a demolulator 237 which is also connected to the generator 233 and has the output 48 (FIG. 1), the stabilized voltage whereacross is dephased by 90° with respect to the stabilized zero-phase voltage.

The herein-disclosed device makes it possible to effect the proposed method of measuring dynamic characteristics of materials, for example, polymers, in a fluid high-elasticity and solid state.

Prior measurement, samples of polymers are molded. Solid polymers are molded into plates or cylinders. Fluid polymers are introduced into conventional cylinder-cylinder or cone-cone systems. High-elasticiy polymers are either introduced into a cylinder-cylinder system or molded into cylinders.

The device for effecting the proposed method of measuring dynamic characteristics of polymers operates as follows.

A molded specimen 2 (FIG. 1) of a polymer is fixed in the holders 3 and 4. The thermocryostatic chamber 1, which has been open prior to this moment, is now shut. The program temperature controller ensures a required temperature of the specimen 2.

A collimated beam from the laser 15 passes through the optical modulator 16 to the mirror 10 and is reflected therefrom onto the mirror 14 of the galvanometer 13. From the mirror 14, the beam proceeds to the mirror 10 and is reflected therefrom onto the prism 17.

In the initial (zero) position of the actuating coil 9 and the galvanometer 13, the beam is reflected from the facets of the prism 17 back to the mirror 10. In this position, the photocells 18 and 19 are dimmed, so there is no voltage across the common load resistor 22. The potentiometer 21 is designed to level out the conversion conductance of the photocells 18 and 19.

The amplitude of oscillations of the galvanometer 13 is set by the precision attenuator comprising the potentiometer 35 with the isolation operational amplifier 38, while the frequency of its oscillations is set by the infra-low frequency oscillator 32, the stabilized zero-phase voltage from the output 33 thereof being applied, via the potentiometer 35, the resistor 37 and the operational amplifier 38, to the galvanometer 13.

Following a deflection of the galvanometer 13 through a certain angle with respect to its initial position, the beam partially passes through the prism 17 and is caught by one of the photocells 18 and 19, depending upon the sense of the rotation of the mirror 14 of the galvanometer 13.

An a.c. voltage appears across the common load resistor 22. This voltage is applied to the output 57 (FIG. 2) of the a.c. voltage amplifier 23.

The first stage of the a.c. voltage amplifier 23 has a high-resistance input and incorporates the field-effect transistor 58. From the load resistor 62, the a.c. voltage is applied via the separating capacitor 63 to the a.c. amplifier 64, is amplified thereby, filtered by the selective circuit comprising the capacitor 67 and the inductance coil 68, both shunted by the resistors 65 and 66, to stabilize the characteristics of the selective circuit, and is then applied to the a.c. amplifier 69. Amplified by the a.c. voltage amplifier 69, the voltage is applied via the separating capacitor 70 to the base of the transistor 71 incorporated into a phase-shifting circuit. The capacitor 78 connected to the load resistor 73 and the variable resistor 77 connected to the load resistor 72 make up a phase-shifting circuit. The alternating voltage from the phase-shifting circuit is applied via the separating capacitor 79 to the a.c. amplifier 80 loaded in the output transformer 81 and having its output 82 connected to the input 88 (FIG. 3) of the demodulator 24. The variable resistor 77 (FIG. 2) sets a phase of the voltage across the output 82, which is equal to the phase of the reference voltage applied to the input 85 (FIG. 3) of the demodulator 24 from a medium-frequency generator (not shown) which also energizes the optical modulator 16 (FIG. 1).

The voltage applied to the input 85 (FIG. 3) of the demodulator 24 is transformed by the transformer 84 and is applied via the ballast resistors 93 and 101 to both fourarm diode bridges which perform the function of diode switches.

For example, if the four-arm diode bridge comprising the diodes 86 through 89, the resistors 90, 91 and the potentiometer 92 is rendered conducting at a certain moment of time by the reference voltage of the medium-frequency generator, i.e. if a current flows through the ballast resistor 93 and said four-arm diode bridge, the other four-arm diode bridge comprising the diodes 94 through 97, the resistors 98, 99 and the potentiometer 100 is non-conducting, i.e. there is no current through the load ballast resistor 101.

On the contrary, if the reference voltage of the medium-frequency generator renders the four-arm diode bridge comprising the diodes 86 through 89, the resistors 90, 91 and the potentiometer 92 non-conducting, the other four-arm diode bridge comprising the diodes 94 through 97, the resistors 98, 99 and the potentiometer 100 at this moment of time is made conducting by the reference voltage of the medium-frequency generator.

The voltage applied to the input 83 of the demodulator 24 from the output 82 (FIG. 2) of the a.c. voltage amplifier 23, which is cophasal to or opposite in phase with the reference voltage, depending upon which of the photocells 18 (FIG. 1) or 19 is illuminated, flows through the four-arm diode bridges and is rectified; as a result, a positive voltage appears across the output 102 (FIG. 3) if the voltage applied to the input 83 of the demodulator 24 is cophasal with the reference voltage across the input 85, and a negative voltage appears across the output 102 if the voltage applied to the input 83 of the demodulator 24 is opposite in phase to the reference voltage across the input 85.

The rectified voltage from the output 102 (FIG. 3) of the demodulator 24 is applied to the input 103 (FIG. 4) of the d.c. voltage amplifier 25.

This voltage passes via the switch 105 to the amplitude-and-phase correction circuit comprising the resistors 119, 120, 121, 122, 123, 124, 125, 126, 127, 128, 129, 130, 131, 132, 133 and the capacitors 107, 108, 109. 110, 111, 112, 113, 114, 115, 116, 117, 118 in the input circuit of the operational amplifier 104 and the resistor 134 in its feedback circuit in the case of measuring dynamic characteristics of a fluid polymer, or comprising the resistors 137, 138, 139, 140 and the capacitors 135 and 136 in the input circuit of the operational amplifier 104 and the parallel-connected resistor 141 and capacitor 142 in its feedback circuit in the case of measuring dynamic characteristics of a solid polymer, or comprising the resistors 151, 152, 153, 154, 155, 156, 157, 158, 159, 160, 161, 162 and the capacitors 143, 144, 145, 146, 147, 148, 149, 150 in the input circuit of the operational amplifier 104 and the resistor 163 and the capacitor 164 in its feed-back circuit in the case of measuring dynamic characteristics of a high-elasticity polymer. The circuits for the amplitude and phase correction of the voltage, which is proportional to the control current, serve to ensure an accurate following up of oscillations of the galvanometer 13 by the actuating coil 9.

The voltage from the output 165 of the d.c. voltage amplifier 25 is applied via the resistor 27 (FIG. 1) to the operational amplifier 28 which serves to match the input and output electric circuits. The current passing through the resistor 29, which is proportional to the voltage across the output of the operational amplifier 28, is applied to the summing amplifier 30, across the output whereof there appears a voltage proportional to that current.

That voltage initiates a current through the actuating coil 9, which interacts with the uniform field of the permanent magnet 11 and produces a torque applied through the rod 8 and the holder 4 to the specimen 2. As a result of the torque, the actuating coil 9 turns in the direction of the reduction of the displacement angle between the actuating coil 9 and the galvanometer 13, or, which is the same, between the mirrors 10 and 14.

From the output 165 (FIG. 4) of the d.c. voltage amplifier 25, the voltage, which is proportional to the control current flowing through the actuating coil 9, is also applied to the input 166 (FIG. 5) of the analyzer 26. This voltage is amplified by the operational amplifier 167 and inverted by the operational amplifier 168. From the operational amplifiers 167 and 168, the opposite-phase voltages are applied to the contacts 187 of the relay 175 and, simultaneously, to the contacts 210 of the relay 176. The switching of the contacts 187 and 210 of the relays 175 and 176 is synchronous with the frequency of the oscillator 32 (FIG. 1), the switching of the contacts 187 (FIG. 5) of the relay 175 being cophasal with the stabilized zero-phase voltage across the output 33 (FIG. 1) of the oscillator 32, whereas the switching of the contacts 210 (FIG. 5) of the relay 176 is cophasal with the stabilized voltage across the output 48 FIG. 1) of the oscillator 32, displaced by 90° with respect to the stabilized zero-phase voltage. There occurs a fullwave rectification of the voltage proportional to that across the output 165 (FIG. 4) of the amplifier 25.

The voltage across the output 165 of the amplifier 25 has a real component, which is in phase with the stabilized voltage across the output 33 of the oscillator 32, and an imaginary component, which is in phase with the stabilized voltage across the output 48 of the oscillator 32. The direct component of the rectified voltage applied to the switch 188 (FIG. 5) is proportional to the real component of the voltage across the output 165 (FIG. 4), whereas the direct component of the voltage across the switch 221 (FIG. 5) is proportional to the imaginary component of the voltage across the output 165 (FIG. 4) of the d.c. voltage amplifier 25; consequently, these are proportional to the components of the control current flowing through the actuating coil 9 (FIG. 1).

The relay 175 (FIG. 5) is connected to the load circuit of the operational amplifier 181 which functions as a null indicator, i.e. a former of a rectangular voltage which is in phase with the sinusoidal voltage across the input 186 of the amplifier 181, whose input 186 is connected to the output 33 (FIG. 1) of the infralow frequency oscillator 32.

At the moment of the sinusoidal voltage being applied to the input 186, the shape of the output voltage of the operational amplifier 181 is close to rectangular. This voltage is applied to the relay 175 switching it in phase with the voltage applied to the input 186.

Similarly, switched in phase with the voltage applied to the input 205 from the output 48 (FIG. 1) of the infralow frequency oscillator 32 is the relay 176 (FIG. 5) which is the load of the operational amplifier 204 whose operating conditions are identical to those of the operational amplifier 181.

The voltage from the outputs of thee operational amplifiers 181 and 204 are applied to the counters 177 and 178 of the alternations of the stabilized voltage of the oscillator 32, respectively, which control the operation of the relays 203 and 226 and the digital voltmeters 179 and 180.

Following each period of the voltage of the oscillator 32 (FIG. 1), there occurs a change in the voltages integrated over that period across the outputs of the integrators incorporating the operational amplifiers 173 (FIG. 5) and 174, and a discharge of the capacitors 196, 197, 198, 199, 200, 201 and 219, 220, 221, 222, 223 in the feedback circuits of the operational amplifiers 173 and 174, respectively, by means of the contacts 202 of the relay 203 and the contacts 225 of the relay 226.

The switches 188 and 211 commutate the resistors 189, 190, 191, 192, 193, 194 and the resistors 212, 213, 214, 215, 216, 127, respectively, while the switches 195 and 218 commutate the capacitors 196, 197, 198, 199, 200, 201 and the capacitors 219, 220, 221, 222, 223, 224, respectively. These commutations are necessary to match the integration time constant with the frequency of the infralow frequency oscillator 32 (FIG. 1).

Figure 6:
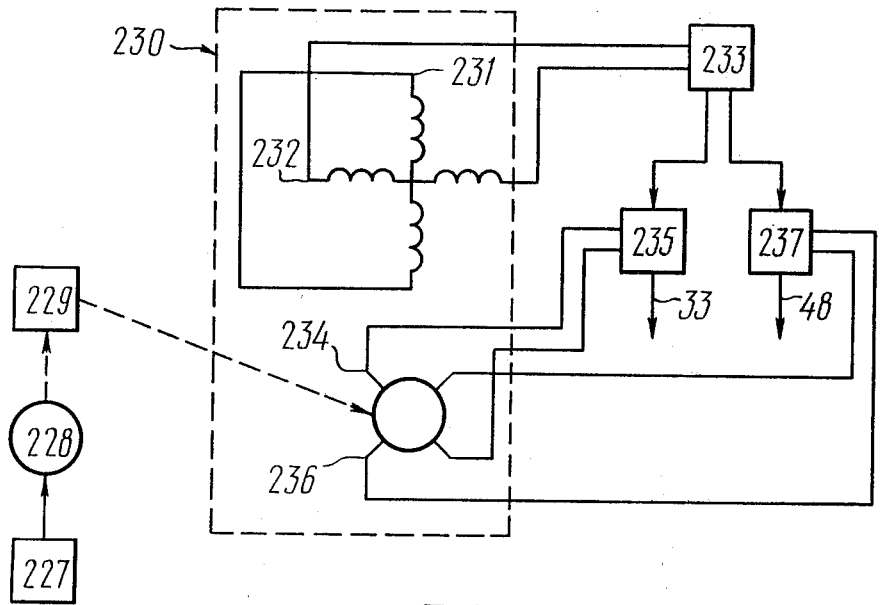
FIG. 6 is an electric circuit of the infralow frequency oscillator of the device, in accordance with the invention.
Figure 7:
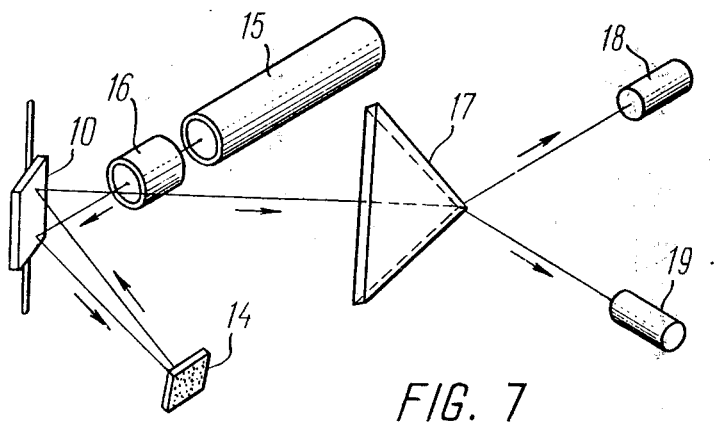
FIG. 7 is an isometric representation of the optical system of the device, in accordance with the invention.

The infralow frequency oscillator 32 comprises the three-phase low-frequency oscillator 227 (FIG. 6). Connected to the oscillator 227 is the synchronous hysteresis motor 228 which actuates the rotor of the rotary sine-consine transformer 230. The stator winding 232 of the rotary sine-cosine transformer 230 is energized by the stable-amplitude voltage from the oscillator 233 which also generates reference voltages for the phase-sensitive demodulators 235 and 237.

The sine rotor winding 234 of the rotary transformer 234 is connected to the phase-sensitive demodulator 235, across the output 33 whereof there appears a stabilized zero-phase voltage, whose frequency is proportional to the rotational speed of the rotor of the rotary transformer.

The cosine rotor winding 236 is connected to the demodulator 237, across the output 48 whereof there appears a stabilized voltage dephased by 90° with respect to the stabilized voltage dephased by 90° with respect to the stabilized zero-phase voltage.

The infralow-frequency stabilized voltage from the output 33 (FIG. 1) is applied to the precision potentiometer 34 and, from its cursor 40 via the high-resistance resistor 41, to the operational amplifier 42. The switch 47 commutates the resistors 44, 45 and 46 in the feedback circuit of the operational amplifier 42.

Each commutation of the resistors 44, 45 and 46 results in a ten-fold change in the amplification factor of the amplifier 42 and, consequently, in a ten-fold change in the voltage applied to the resistor 43.

From the output 48 of the infralow frequency oscillator 32, the stabilized voltage dephased by 90 with respect to the stabilized zero-phase voltage is applied to the precision potentiometer 49 and from its cursor 49' via the high-resistance resistor 50, to the operational amplifier 51, in the feedgack circuit whereof there are the switch 56 and the resistors 53, 54 and 55. Each commutation of the resistors 53, 54 and 55 results in a 10-fold change in the amplification factor of the amplifier 51 and, consequently, in a 10-fold change in the voltage applied to the resistor 52.

The restoring zero-phase current with a phase of 0°, which, passes via the resistor 43 to the summing operational amplifier, 30 changes smoothly within the tenfold variation range with the aid of the precision potentiometer 34 and in a quantified manner, with the aid of the switch 47.

The restoring current with a phase displaced by 90° with respect to the current with a phase of 0°, which passes via the resistor 52 to the summing operational amplifier 30, changes smoothly within the 10-fold range with the aid of the precision potentiometer 49 and, discretely, with the aid of a switch 56.

The current which flows through the first open circuit for proportional control of the movement of the actuating coil 9 and is proportional to the stabilized zero-phase voltage of the infralow frequency oscillator 32, is applied to the summing amplifier 30 and compensates the real component of the current through the closed follow-up circuit, whereas the current, which flows through the second open circuit for proportional control of the movement of the actuating coil 9 and is proportional to the stabilized voltage displaced in phase by 90° with respect to the stabilized zero-phase voltage, is applied to the summing amplifier 30 and compensates the imaginary component of the current through the closed follow-up circuit.

The precision attenuators select voltages of the open circuits for proportional control of the movement of the actuating coil 9, so that the real and imaginary components of the voltage, which are proportional to the real and imaginary components of the current through the closed followup circuit, be commensurable to each other.

This raises the accuracy of measurement, as the analyzer 26 connected to the infralow frequency oscillator 32 and, via the buffer amplifier and the summing amplifier 30, to the actuating coil 9, which measures the components of the current through the closed follow-up circuit has an operational accuracy which is inversely proportional to the difference between the real and imaginary components of the current.

The proposed method of measuring dynamic characteristics and the device for effecting same make it possible to measure dynamic characteristics of materials in the infralow frequency range below $10^{-3}$ to $10^{-4}$ Hz, substantially cut down operator man hours and raise the accuracy of parameters under measurement.

What is claimed is:

1. A device for measuring dynamic characteristics of materials, comprising a thermocryostatic chamber with a program temperature controller connected thereto, a specimen of a material and two holders for adjusting said specimen inside said thermocryostatic chamber; a rod; a normal stress compensator attached by said rod to said holder of the specimen, for relieving normal stresses in said specimen; a second rod coupled to the second holder of the specimen to transmit a mechanical moment to said specimen; an actuating coil comprised of wire in the form of a loop placed in a uniform field of a permanent magnet to obtain a moment by means of the interaction of the current flowing through said coil and said uniform field of the permanent magnet; a mirror fixed to said actuating coil to follow the rotation of said actuating coil, said actuating coil being rigidly connected to said second rod to transmit a mechanical moment to said rod; an infralow frequency oscillator having an output with a stabilized zero-phase voltage thereacross; a precision attenuator; a galvanometer with a mirror placed in the uniform field of the permanent magnet together with the actuating coil and connected via said precision attenuator to the output of said infralow frequency oscillator with a stabilized zero-phase voltage thereacross to obtain oscillations of said galvanometer at a preset amplitude and frequency; an analyzer connected to said infralow frequency oscillator, a laser; an optical modulator; said mirror of the actuating coil optically associated via said optical modulator with said laser to obtain a collimated beam modulated by a higher frequency, said mirror also being optically associated with the mirror of said galvanometer; a prism and two differentially connected photocells with a common load, optically associated via said prism and said mirror of the actuating coil with said mirror of the galvanometer to obtain a voltage proportional to the difference between the oscillations of said galvanometer and those of said actuating coil; an a.c. voltage amplifier connected to said common load of the two differentially connected photocells to amplify said voltage proportional to the difference between the angles of rotation of said galvanometer and said actuating coil; a demodulator connected to said a.c. voltage amplifier to obtain a voltage of a preset frequency; a d.c. voltage amplifier with circuits for amplitude and phase correction of the voltage proportional to the control current, connected to the demodulator and the analyzer; a buffer amplifier with its input and output electric circuits connected to said d.c. voltage amplifier for matching said input and output electric circuits; a summing amplifier connected to said buffer amplifier to receive said control current; said summing amplifier being connected to said actuating coil to transmit said control current through the actuating coil; said galvanometer with the mirror, laser, optical modulator, mirror of the actuating coil , prism, two differentially connected photocells with the common load and the series-connected a.c. voltage amplifier, demodulator, d.c. voltage amplifier, buffer amplifier, summing amplifier and actuating coil comprising a closed followup circuit, said infralow frequency oscillator having an output with a stabilized zero-phase voltage thereacross and the precision attenuator comprising means for setting the amplitude and frequency of oscillations of said specimen.

2. A device as claimed in claim 1, including a second precision attenuator connected to said output of said infralow frequency oscillator with a stabilized zero-phase voltage thereacross to change said output voltage, said infralow frequency oscillator, said summing amplifier being connected to said second precision attenuator to receive current restoring the real component of the control current and proportional to the changed voltage from the output of said precision atgenuator, and said actuating coil being connected to said summing amplifier for the total current to be transmitted through said actuating coil and comprising an open circuit for proportional control of the movement of the actuating coil.

3. A device as claimed in claim 2, wherein said infralow frequency oscillator has another output, the stabilized voltage across said other output being displaced in phase by 90° with respect to the stabilized zerophase voltage, and a third precision attenuator connected to said output of said infralow frequency oscillator, the stabilized voltage whereacross being displaced in phase 90° with respect to the stabilized zero-phase voltage, for changing said output voltage of said infralow frequency oscillator, said summing amplifier being connected to said third precision attenuator to receive current restoring the imaginary component of the control current and proportional to the changed voltage across the output of said third precision attenuator, said actuating coil being connected to said summing amplifier for the total current to be transmitted through said actuating coil and comprising a second open circuit for proportional control of the movement of the actuating coil, the total current flowing through said actuating coil and interacting with said uniform field of the permanent magnet, a mechanical moment being produced which is applied to said specimen, thereby ensuring oscillations of the specimen at a preset amplitude and frequency and proportional to the stabilized zero-phase voltage of said infralow frequency oscillator.

4. A method of measuring dynamic characteristics of materials in the infralow frequency range, comprising the steps of ensuring oscillations of a specimen of a material at a preset amplitude and frequency by obtaining, in the course of measurement, a control current and converting said control current into a mechanical stress of said specimen of a real and an imaginary component of said control current, discriminating a first time and analyzing said components of said control current, generating two restoring currents, one being in phase and commensurable with said real component of said control current, whereas the other is in phase and commensurable with said imaginary component of said control current, summing said control current and said two restoring currents, converting the total current into a mechanical stress of the specimen for controlling the movement of said specimen for a preset amplitude and frequency, discriminating for a second time the real and imaginary components of said control current, said values of the components of said control current, the values of said restoring currents and the preset amplitude and frequency of the deformation of a material being used, in relation to the shape of said specimen, to calculate dynamic characteristics of the material.

* * * * *